United States Patent
Dekel et al.

(10) Patent No.: US 10,242,548 B2
(45) Date of Patent: Mar. 26, 2019

(54) MEDICAL TOOL PUNCTURE WARNING METHOD AND APPARATUS

(71) Applicant: Biosense Webster (Israel) Ltd., Yokneam (IL)

(72) Inventors: Zvi Dekel, Yaakov (IL); Akram Zoabi, Yokneam (IL); Yaniv Ben Zrihem, Binyamina (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 15/602,818

(22) Filed: May 23, 2017

(65) Prior Publication Data
US 2018/0342144 A1 Nov. 29, 2018

(51) Int. Cl.
G08B 21/00 (2006.01)
G08B 21/18 (2006.01)
A61B 17/34 (2006.01)

(52) U.S. Cl.
CPC ........ G08B 21/182 (2013.01); A61B 17/3401 (2013.01)

(58) Field of Classification Search
CPC .......................... A61B 17/3401; G08B 21/182
USPC ..................................................... 340/686.1
See application file for complete search history.

(56) References Cited

U.S. PATENT DOCUMENTS 4,791,937 A * 12/1988 Wang .................. A61B 10/0283
600/565
9,861,802 B2 * 1/2018 Mickelsen ........... A61B 5/0538
2006/0013523 A1 1/2006 Childers
2009/0318797 A1 12/2009 Hadani
2012/0143006 A1 6/2012 Avitsian
2015/0073245 A1 3/2015 Klimovitch
(Continued)

FOREIGN PATENT DOCUMENTS

WO 98/29033 A1 7/1998
WO 2016028858 A1 2/2016
(Continued)

OTHER PUBLICATIONS

Deepak Bhakta, MD and John M Miller. "Principles of Electroanatomic Mapping", Indian Pacing Electrophysiol J. Jan.-Mar. 2008; 8(1): 32-50.
(Continued)

*Primary Examiner* — Qutbuddin Ghulamali
(74) *Attorney, Agent, or Firm* — Volpe and Koenig, P.C.

(57) ABSTRACT

A conduit puncture alert method and apparatus are provided for a medical instrument having a flexible conduit through which a medical procedure is performed. In one embodiment, the flexible conduit is inserted into a subject. A highest degree of curvature of the conduit within the subject is sensed. A warning signal is then provided upon a condition that a curvature is sensed that exceeds a predetermined limit reflective of a maximum curvature permissible for a selected tool to be inserted through the conduit while avoiding puncturing of the conduit by the selected tool. For example, the method can be conducted with respect to a bronchoscope during a bronchoscopic procedure where a needle tool is to be used and the warning is given with respect to that tool when a conduit curvature is sensed that exceeds a predetermined limit determined with respect to the needle tool.

20 Claims, 2 Drawing Sheets

(56) References Cited

U.S. PATENT DOCUMENTS

2015/0352715 A1* 12/2015 Yanagihara ............... B25J 9/06
                                                        74/89.23
2017/0020612 A1* 1/2017 Kuboi .................... G02B 23/24

FOREIGN PATENT DOCUMENTS

WO    2016032902 A1    3/2016
WO    2016040080 A1    3/2016

OTHER PUBLICATIONS

Extended Search Report issued in corresponding European Patent Application No. 18173524.2 dated Oct. 19, 2018, consisting of 8 pp.

* cited by examiner

MEDICAL TOOL PUNCTURE WARNING METHOD AND APPARATUS

SUMMARY

A conduit puncture alert method and apparatus are provided for a medical instrument having a flexible conduit through which a medical procedure is performed.

In one embodiment, the flexible conduit is inserted into a subject. A highest degree of curvature of the conduit within the subject is sensed. A warning signal is then provided upon a condition that a curvature is sensed that exceeds a predetermined limit reflective of a maximum curvature permissible for a selected tool to be inserted through the conduit while avoiding puncturing of the conduit by the selected tool. For example, the method can be conducted with respect to a bronchoscope during a bronchoscopic procedure where a needle tool is to be used and the warning is given with respect to that tool when a conduit curvature is sensed that exceeds a predetermined limit determined with respect to the needle tool.

Predetermined limits reflective of a respective degree of maximum curvature permissible for a plurality of tools to be inserted through the conduit while avoiding puncturing of the conduit by the tool may be provided. In such case, a warning signal can be provided with respect to each of the plurality of tools upon a condition that a curvature is sensed that exceeds the respective predetermined limit. The warning signal can include a visual warning with respect to each tool during the time a curvature is sensed that exceeds the respective tool's predetermined limit.

The warning signal can includes a warning light, a visual warning display, an audible warning or a combination thereof. The conduit puncture alert method may further include determining the predetermined limit for one or more selected tools.

In another embodiment, a medical instrument is provided having a conduit through which a medical procedure is performed. The conduit is selectively configured for insertion into a subject. A controller is configured to sense the curvature of the conduit in the subject. The controller configured to control a peripheral device to provide a warning signal, upon a condition that a curvature is sensed that exceeds a predetermined limit reflective of a maximum curvature permissible for a selected tool to be inserted through the conduit while avoiding puncturing of the conduit by the selected tool.

There can be a plurality of tools usable with the medical instrument. Each tool can have a respective predetermined limit reflective of a respective degree of maximum curvature permissible for the tool to be inserted through the conduit while avoiding puncturing of the conduit by the tool. The controller can be configured to control the peripheral device to provide a warning signal with respect to each of the plurality of tools upon a condition that a curvature is sensed that exceeds the respective predetermined limit.

The medical instrument can be configured as a bronchoscope. In such case, there can be a plurality of needle tools usable with the bronchoscope, each having a different predetermined limit reflective of a respective degree of maximum curvature permissible for the respective needle tool to be inserted through the conduit while avoiding puncturing of the conduit by the needle tool. The controller can then be configured to control the peripheral device to provide a warning signal with respect to each of the plurality of needle tools upon a condition that a curvature is sensed that exceeds the respective predetermined limit. The peripheral device can include a display configured with the controller to provide a visual warning with respect to each needle tool during the time a curvature is sensed that exceeds the respective needle tool's predetermined limit. The peripheral device can be configured to provide the warning signal as a warning light, a visual warning display, an audible warning or a combination thereof.

Other object and advantages of the invention will be apparent to those skilled in the art from the drawings and following detailed description.

DETAILED DESCRIPTION OF THE PREFERRED EMBODIMENT(S)

Figure 1:
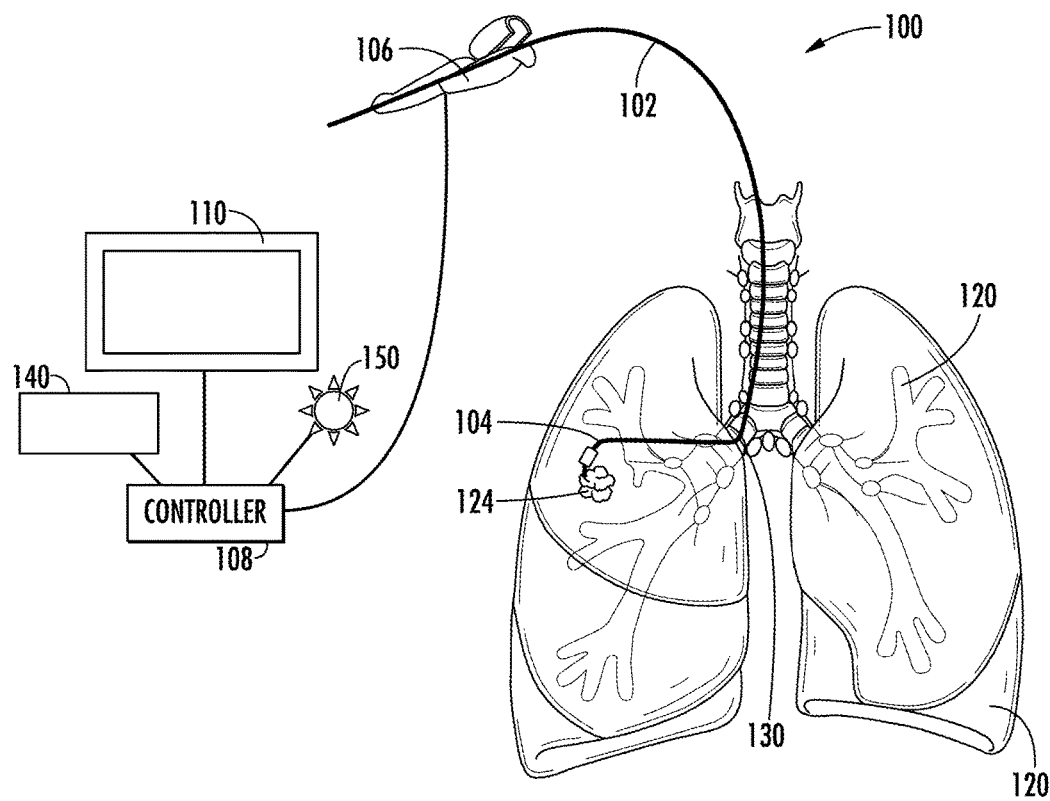
FIG. 1 is a schematic illustration of a bronchoscope and associated components during a bronchoscopic procedure utilizing the warning system in accordance with the teachings of the present invention.

The present invention is related to the prevention of punctures in the flexible conduits of medical instruments due to the insertion of tools such as, for example, the insertion of a hollow needle in the flexible conduit of a bronchoscope during a bronchoscopic procedure.

A variety of medical instruments have been developed for non-invasive diagnosis and surgery that employ the insertion of a flexible conduit into a subject through which a camera, tool or other implement can be inserted and operated at the conduit's distal end that has been selectively positioned at a desired location within the subject. Many types of medical instruments operate in such a manner, including, for example, bronchoscopes, endoscopes, anoscopes, sigmoidoscopes, rhinolaryngoscopes and laryngoscopes.

Developments in the control of the insertion of medical instrument flexible conduits enable physicians to visually explore internal structures and abnormalities of a subject non-invasively or with minimal invasiveness. With modern medical instruments, the distal end of an instrument's flexible conduit can be inserted proximate, for example, a tumor by following natural structures of the subject's body such as blood vessels and air passages. A physician can not only see the tumor or other item of interest in this manner by virtue of a camera relaying video from the distal end of the conduit, but can also perform medical procedures through the introduction of a tool through the conduit. For example, the selected tool may be remotely operated to take a tissue sample at the selectively located distal end of the conduit of the medical instrument. Examples of commonly available tools include hollow needles, flexible cup biopsy forceps, and nylon brushes.

Transbronchial needle aspiration (TBNA) is one example procedure where a needle is employed as a tool for a bronchoscope. TBNA is used for diagnosis and staging of bronchial diseases, including mediastinal or peripheral pathologies, subcarinal and parabronchial nodes and parenchymal abnormalities. Standard TBNA techniques may use, for example, a 21-gauge cytology needle or a 19-gauge histology needle together in conjunction with a flexible bronchovideoscope.

When a pulmonologists performs TBNA or another bronchoscopic procedure on a subject, the flexible conduit of the bronchoscope is used to navigate inside the airways of the lung to see abnormalities. To accommodate navigation within the lung, the bronchoscope's flexible conduit bends such that significant degrees of curvature of the conduit may be introduced.

Fiber optic, magnetic and any other shape sensing technologies have been used to assist with the conduit insertion and to provide real time data and displays representing the position of the portion of the conduit that has been introduced into the subject. See, for example, US Patent Publication No. 20060013523, Principles of Electroanatomic Mapping, Deepak Bhakta, MD and John M Miller, Indian Pacing Electrophysiol J. 2008 January-March; 8(1): 32-50, and International Publication No. WO 2016/028858. Through these techniques, precise calculations of the path and curvature of the conduit in situ are readily made during the medical procedure.

The inventors have recognized that when, for example, a pulmonologists performs a bronchoscopic procedure requiring a tool, the bronchoscope's flexible conduit may become curved in such a manner that when the physician inserts a tool, the tool may puncture the sheath-construction of the flexible conduit. When the sheath portion of a bronchoscope's flexible conduit is damaged, the repair can be very expensive and the instrument may even be discarded by the physician. Accordingly, the inventors have recognized that there is a need for improved bronchoscopes and similar medical instruments that warn when a tool, such as a needle, forceps or brush, is about to puncture the flexible conduit of the instrument.

With reference to FIG. 1, a bronchoscope 100 is illustrated as an example of a type of medical instrument that employs a flexible conduit for which the invention is applicable. The example bronchoscope 100 includes a flexible conduit 102 which has a distal end 104 where a camera and associated light emitter are disposed.

The example bronchoscope 100 includes a robotic handle 106 and associated controller 108 and video display 110 that enable a physician or other operator to selectively and precisely insert the distal end 104 of the flexible conduit 102 to a desired location within the air passages 120 of the lungs 122 of a subject. For example, FIG. 1 illustrates the result of the insertion of the flexible conduit 102 to locate the distal end 104 of the flexible conduit 102 proximate a tumor 124.

The display is preferably configured to display images from the camera of the distal end 104 to assist the physician in navigating through the air passages 120 while inserting the flexible conduit 102 to reach the desired location using the robotic handle 106. The robotic handle 106 is controlled by the controller 108 to effectuate the insertion movement directed by the physician.

The flexible conduit 102 preferably includes an optic fiber which may be part of the signaling components for the camera or light emitter of the distal end 104. The controller 108 is preferably configured with fiber optic sensing to generate data via the optic fiber to assist in the control of the flexible conduit and the display of a representation of the conduit location within the subject's airways as a portion of displayed graphics on the display 110 during use. The fiber optic sensing performed by the controller 108 provides precise calculations of the path and curvature of the conduit in situ during bronchoscopic procedure.

Figure 2A:
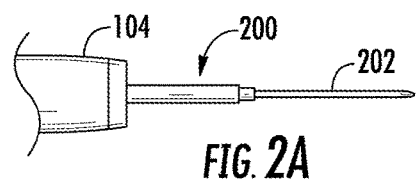
FIGS. 2(A)-2(C) are illustrations of example tools usable with the bronchoscope of FIG. 1.
Figure 2B:
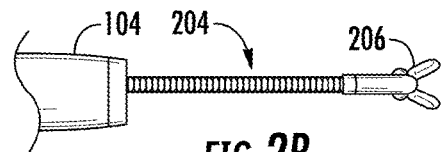
Figure 2C:
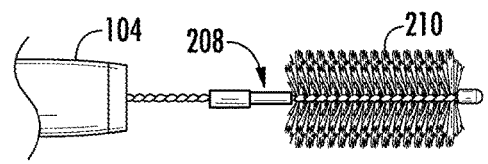

A variety of tools of various shapes and sizes can be provided for use during a selected bronchoscopic procedure through the flexible conduit. For example, FIG. 2(A) illustrates a hollow needle tool 200 that has been disposed in the flexible conduit 102 with the tool's needle 202 extending from the distal end 104. FIG. 2(B) illustrates a biopsy forceps tool 204 that has been disposed in the flexible conduit 102 with the tool's forceps 206 extending from the distal end 104. FIG. 2(C) illustrates a brush tool 208 that has been disposed in the flexible conduit 102 with the tool's brush 210 extending from the distal end 104. The degree of extension of the tools from the distal end 104 of the conduit 102 as illustrated in FIGS. 2(A)-(C) is exaggerated for illustration purposes only and is not reflective of their actual use during a bronchoscopic procedure where only the operating end of the tool is usually extended from the distal end 104 of the flexible conduit 102.

As illustrated in FIG. 1, the flexible conduit 102 of the example bronchoscope 100 can bend to accommodate navigation within the air passages 120 of a subject's lung 122. As a result, the bronchoscope may have an area of curvature, such as illustrated at location 130 of the flexible conduit 102, through which the insertion of a tool will puncture or otherwise damage the flexible conduit 102. When the flexible conduit 102 the bronchoscope 100 is punctured or otherwise damaged, the repair can be very expensive. The result of puncture or damage can lead to the instrument being discarded.

To prevent puncture or other damage to the flexible conduit 102 due to the insertion of a tool there through during a medical procedure, the controller 108 is configured to utilize the optic sensing data of the path and curvature of the conduit 102 in situ during the procedure. Preferably, a memory 140, is provided, which may be integral with the controller 108, wherein data is stored with respect to predetermined limits reflective of a maximum curvature permissible for respective tools to be inserted through the conduit 102 while avoiding puncturing of the conduit by the respective tool. Limit data may be stored with respect to all tools available for use at the time of employing the bronchoscope in a medical procedure or just for one or more selected tools, such as for needle tools that are most likely to result in punctures.

Preferably, the controller compares the highest degree of curvature experienced by any portion of the flexible conduit 102 with the stored predetermined limits. When such a comparison results in the sensed curvature of the flexible conduit 102 exceeding one or more of the predetermined limits, the controller 108 activates a warning signal. This is preferably done on a continuous basis during the insertion of the flexible conduit 102. However, the controller can be configured to perform such comparisons only when the insertion motion is stopped.

The warning signal activated by the controller 108 can be with respect to an auxiliary device 150, such as light or audio device and/or can be represented on the display 100. An example is provided with reference to FIG. 3, where the controller 108 is configured to control the display 110 to display in a split screen mode. There, for example, screen portion 302 is utilized to display the images generated by the distal end camera within the subject, screen portion 304 is used to display a graphic illustration of the flexible conduit as currently disposed within the subject, screen portion 306 is utilized to display current biometric data of the subject, and screen portion 308 is used to display insertion warning data.

Figure 3:
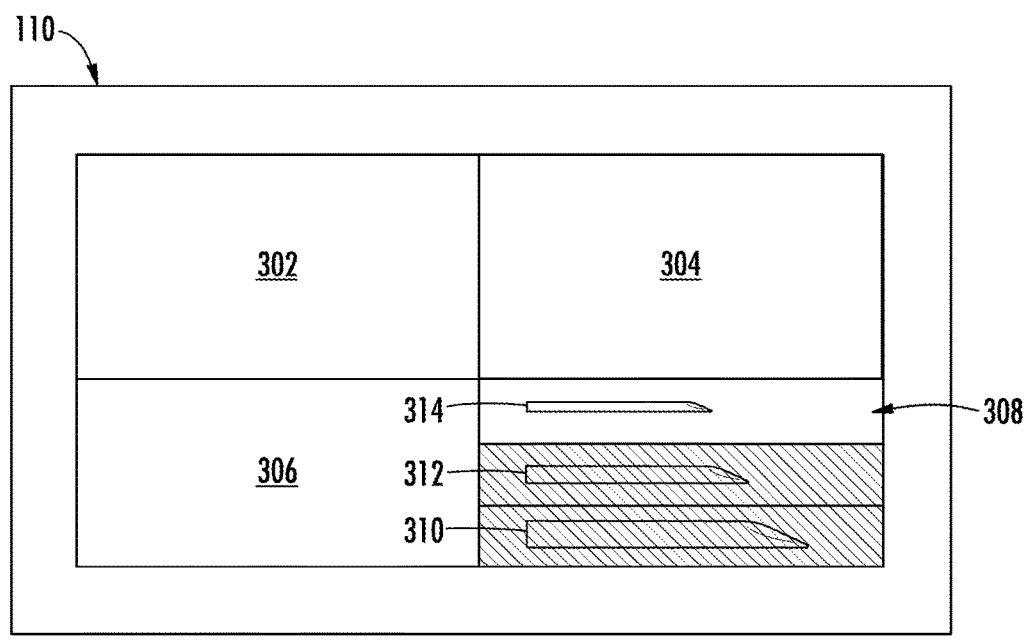
FIG. 3 is a schematic illustration of a split screen display associated with the bronchoscope of FIG. 1.

In the FIG. 3 example, warning data is graphically displayed on display 110 in screen portion 308 with respect to three different size needle tools regarding the curvature of the flexible conduit 102 as disposed within the lungs 122 of a subject as depicted in FIG. 1. The controller 108, using the sensing data generated by optic sensing, has determined that the highest degree of curvature of the flexible conduit 102 is at location 130, and that the sensed highest degree of conduit curvature exceeds the predetermined limits with respect to two larger needle tools represented as screen images 310 and 312, but has not exceeded the predetermined limit with respect to a smaller needle tool represented as screen images 314. In such example, the controller 108 causes the images 310 and 312 to be represented with a warning indicated as, for example, a red background (indicated by shading), but retains, for example, a green background with respect to the image 314 thereby indicating that the smaller needle tool may be used without damaging the bronchoscope 100 disposed as illustrated in FIG. 1.

Predetermined limits reflective of a maximum curvature permissible for respective tools to be inserted through the conduit 102 can be calculated using precise dimension of the operative end of the respective tool in comparison with the conduit bore size. For example, parameters taken into account in determining a maximum permissible curvature for a needle tool include:

1. The length of the needle;
2. The diameter of the working channel in the bronchoscope;
3. The max curvature of the bronchoscope in partitions with the needle's length in a moving window—for example if the needle is 5 mm consider all the possibilities of consecutive 5 mm length sections of the bronchoscope; and
4. The elasticity of the tool that carries the needle.

Where such theoretical computations are made, it is preferred to test the results by insertion of the tool in an example flexible conduit of the given conduit.

One can, however, determine the limits through physical testing by:
positioning an example conduit of the given size to have a progressively increasing arcuate curvature orientation,
inserting the tool until it begins to puncture or otherwise damage the sample conduit, and
using the degree of curvature at the point of puncture within the conduit to set the limit for that tool.

Figure 4:
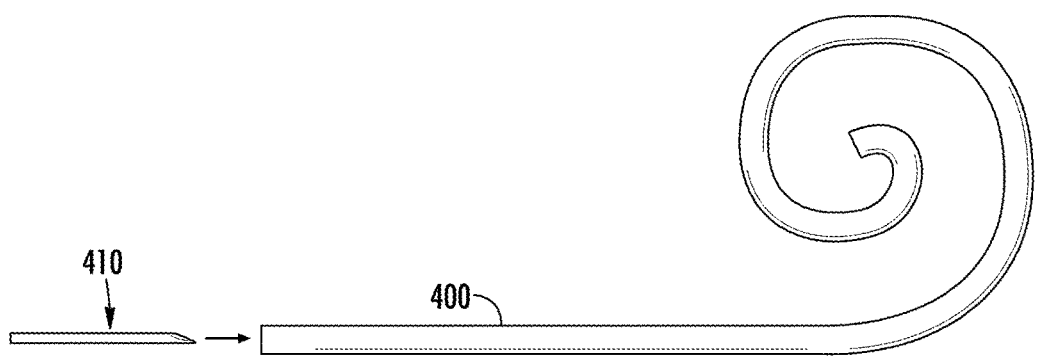
FIG. 4 is a schematic diagram of a method of making a determination of predetermined limits of curvature for the utilization tools with the bronchoscope of FIG. 1.

This is, for example, illustrated in FIG. 4 where a sample conduit 400 is provided in an orientation having a progressively increasing curvature. A needle tool 410 is inserted into the sample conduit until begins to puncture the conduit 400. At the point of puncture of the conduit 400, the curvature is noted and the limit is preferably determined with respect to needle tool 410 to be that amount of curvature less a desired safety margin.

Although the invention is described with respect to the example bronchoscope discussed above, it is applicable to any type of medical instrument that utilizes a flexible conduit through which tools are inserted during medical procedures.

What is claimed is:

1. A conduit puncture alert method for a medical instrument having a flexible conduit through which a medical procedure is performed comprising:
    inserting the conduit into a subject;
    sensing curvature of the conduit within the subject;
    providing a puncture warning signal with respect to a selected tool upon a condition that a curvature is sensed that exceeds a predetermined limit reflective of a maximum curvature permissible for the selected tool to be inserted through the conduit while avoiding puncturing of the conduit by the selected tool.

2. The conduit puncture alert method according to claim 1, where there are a plurality of tools usable with the medical instrument, each tool having a respective predetermined limit reflective of a respective maximum curvature permissible for the tool to be inserted through the conduit while avoiding puncturing of the conduit by the tool, wherein:
    a puncture warning signal is provided with respect to each of the plurality of tools upon a condition that a curvature is sensed that exceeds the respective predetermined limit.

3. The conduit puncture alert method according to claim 1, where the medical instrument is a bronchoscope and the selected tool is a needle tool wherein the method is conducted during a bronchoscopic procedure.

4. The conduit puncture alert method according to claim 3, where there are a plurality of different size needle tools usable with the bronchoscope, each needle tool having a different predetermined limit reflective of a respective maximum curvature permissible for the respective needle tool to be inserted through the conduit while avoiding puncturing of the conduit by the needle tool, wherein:
    a puncture warning signal is provided with respect to each of the plurality of needle tools upon a condition that a curvature is sensed that exceeds the respective predetermined limit.

5. The conduit puncture alert method according to claim 4, wherein the puncture warning signal includes a display that includes a visual warning with respect to each needle tool during the time a curvature is sensed that exceeds the respective needle tool's predetermined limit.

6. The conduit puncture alert method according to claim 4, wherein the puncture warning signal includes a warning light, a visual warning display, an audible warning or a combination thereof.

7. The conduit puncture alert method according to claim 4 further comprising determining the respective predetermined limit for each needle tool.

8. The conduit puncture alert method according to claim 1, wherein the puncture warning signal includes a display that includes a visual warning during the time a curvature is sensed that exceeds the tool's predetermined limit.

9. The conduit puncture alert method according to claim 1, wherein the puncture warning signal includes a warning light, a visual warning display, an audible warning or a combination thereof.

10. The conduit puncture alert method according to claim 1 further comprising determining the predetermined limit for the selected tool.

11. A medical instrument having comprising:
    a conduit through which a medical procedure is performed;
    the conduit selectively configured for insertion into a subject;
    a controller configured to sense curvature of the conduit in the subject;
    a peripheral device;
    the controller configured to control the peripheral device to provide a puncture warning signal with respect to a selected tool, upon a condition that a curvature is sensed that exceeds a predetermined limit reflective of a maximum curvature permissible for the selected tool to be inserted through the conduit while avoiding puncturing of the conduit by the selected tool.

12. The medical instrument according to claim 11, where there are a plurality of tools usable with the medical instrument, each tool having a respective predetermined limit reflective of a respective maximum curvature permissible for the tool to be inserted through the conduit while avoiding puncturing of the conduit by the tool, wherein:
the controller is configured to control the peripheral device to provide a puncture warning signal with respect to each of the plurality of tools upon a condition that a curvature is sensed that exceeds the respective predetermined limit.

13. The medical instrument according to claim 11 configured as a bronchoscope where the selected tool is a needle tool.

14. The medical instrument according to claim 13, where there are a plurality of needle tools usable with the bronchoscope, each needle tool having a different predetermined limit reflective of a respective maximum curvature permissible for the respective needle tool to be inserted through the conduit while avoiding puncturing of the conduit by the needle tool, wherein:
the controller is configured to control the peripheral device to provide a puncture warning signal with respect to each of the plurality of needle tools upon a condition that a curvature is sensed that exceeds the respective predetermined limit.

15. The medical instrument according to claim 14, wherein the peripheral device includes a display configured with the controller to provide a visual warning with respect to each needle tool during the time a curvature is sensed that exceeds the respective needle tool's predetermined limit.

16. The medical instrument according to claim 14, wherein the peripheral device is configured to provide the puncture warning signal as a warning light, a visual warning display, an audible warning or a combination thereof.

17. The medical instrument according to claim 13, wherein the peripheral device includes a display configured with the controller to provide a visual warning with respect to the needle tool during the time a curvature is sensed that exceeds the needle tool's predetermined limit.

18. The medical instrument according to claim 13, wherein the peripheral device is configured to provide the puncture warning signal as a warning light, a visual warning display, an audible warning or a combination thereof.

19. The medical instrument according to claim 11, wherein the peripheral device includes a display configured with the controller to provide a visual warning with respect to the selected tool during the time a curvature is sensed that exceeds the predetermined limit.

20. The medical instrument according to claim 11, wherein the peripheral device is configured to provide the puncture warning signal as a warning light, a visual warning display, an audible warning or a combination thereof.

* * * * *

UNITED STATES PATENT AND TRADEMARK OFFICE
CERTIFICATE OF CORRECTION

PATENT NO. : 10,242,548 B2
APPLICATION NO. : 15/602818
DATED : March 26, 2019
INVENTOR(S) : Zvi Dekel et al.

It is certified that error appears in the above-identified patent and that said Letters Patent is hereby corrected as shown below:

In the Specification

In Column 1, Line 32, after "can", delete "includes" and insert therefore --include--.

In the Claims

In Column 6, Line 55, Claim 11, after "instrument", delete "having.".

Signed and Sealed this
Eighteenth Day of June, 2019

Andrei Iancu
*Director of the United States Patent and Trademark Office*